US012004775B2

(12) United States Patent
Li et al.

(10) Patent No.: US 12,004,775 B2
(45) Date of Patent: Jun. 11, 2024

(54) CORONARY SINUS-ANCHORED SHEATH FOR DELIVERY OF HIS BUNDLE PACING LEAD

(71) Applicant: PACESETTER, INC., Sylmar, CA (US)

(72) Inventors: Wenwen Li, San Jose, CA (US); Gene A. Bornzin, Simi Valley, CA (US); Didier Theret, Porter Ranch, CA (US); Luke C. McSpadden, Los Angeles, CA (US); Nima Badie, Berkeley, CA (US)

(73) Assignee: PACESETTER, INC., Sylmar, CA (US)

( * ) Notice: Subject to any disclaimer, the term of this patent is extended or adjusted under 35 U.S.C. 154(b) by 779 days.

(21) Appl. No.: 17/071,847

(22) Filed: Oct. 15, 2020

(65) Prior Publication Data

US 2021/0085986 A1    Mar. 25, 2021

Related U.S. Application Data

(63) Continuation of application No. 15/900,558, filed on Feb. 20, 2018, now Pat. No. 10,850,108.
(Continued)

(51) Int. Cl.
*A61B 17/34* (2006.01)
*A61M 25/00* (2006.01)
(Continued)

(52) U.S. Cl.
CPC ....... *A61B 17/3468* (2013.01); *A61M 25/007* (2013.01); *A61M 25/0147* (2013.01);
(Continued)

(58) Field of Classification Search
CPC ............. A61B 17/3468; A61N 1/372; A61N 1/37205; A61N 2001/0585; A61M 25/0029; A61M 25/003; A61M 25/0133; A61M 25/0147; A61M 2025/0095; A61M 2025/0096; A61M 2025/018
See application file for complete search history.

(56) References Cited

U.S. PATENT DOCUMENTS 6,066,125 A    5/2000 Webster, Jr.
6,723,069 B1    4/2004 Weldon et al.
(Continued)

FOREIGN PATENT DOCUMENTS

WO    WO-2007147058 A2 * 12/2007    ............ A61B 5/01

*Primary Examiner* — Sarah W Aleman
(74) *Attorney, Agent, or Firm* — Womble Bond Dickinson (US) LLP

(57) ABSTRACT

Disclosed herein is a catheter for delivering an implantable medical lead to an implantation site near an ostium leading to a proximal region of a coronary sinus. The catheter includes a distal end, a proximal end opposite the distal end, a tubular body extending between the distal and proximal ends, an atraumatic fixation structure defining a distal termination of the distal end, and a lead receiving lumen. The atraumatic fixation structure is configured to enter the ostium and passively pivotally anchor with the proximal region of the coronary sinus. The lead receiving lumen extends along the tubular body from the proximal end to an opening defined in a side of the tubular body near the distal end and proximal the atraumatic fixation structure.

18 Claims, 6 Drawing Sheets

Related U.S. Application Data

(60) Provisional application No. 62/468,829, filed on Mar. 8, 2017.

(51) Int. Cl.
*A61M 25/01* (2006.01)
*A61N 1/372* (2006.01)
*A61B 5/321* (2021.01)
*A61N 1/05* (2006.01)
*A61N 1/362* (2006.01)
*A61N 1/39* (2006.01)

(52) U.S. Cl.
CPC .......... *A61N 1/37205* (2013.01); *A61B 5/321* (2021.01); *A61M 2025/0042* (2013.01); *A61M 2025/0095* (2013.01); *A61M 2025/0096* (2013.01); *A61M 25/0102* (2013.01); *A61M 25/0136* (2013.01); *A61N 1/0563* (2013.01); *A61N 1/0573* (2013.01); *A61N 2001/0585* (2013.01); *A61N 1/3622* (2013.01); *A61N 1/39622* (2017.08)

(56) References Cited

U.S. PATENT DOCUMENTS

| | | |
|---|---|---|
| 7,056,314 B1 | 6/2006 | Florio et al. |
| 8,315,713 B2 * | 11/2012 | Burnes ............... A61N 1/36053 607/116 |
| 2006/0247750 A1 * | 11/2006 | Seifert ................ A61N 1/056 607/122 |
| 2007/0225750 A1 | 9/2007 | Ren et al. |
| 2013/0281925 A1 * | 10/2013 | Benscoter ............ A61B 1/0125 604/95.04 |
| 2016/0220741 A1 | 8/2016 | Garrison et al. |
| 2017/0246427 A1 * | 8/2017 | Gurley ................ A61B 17/22 |

* cited by examiner

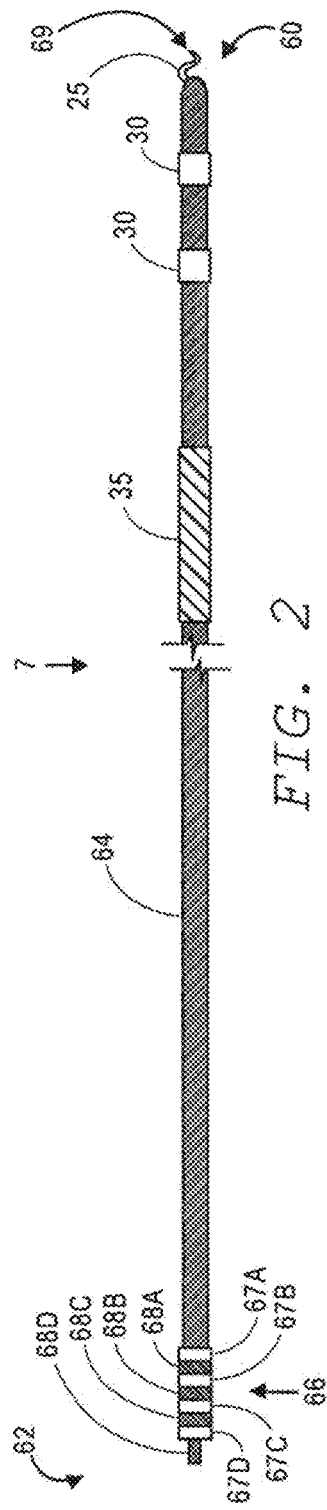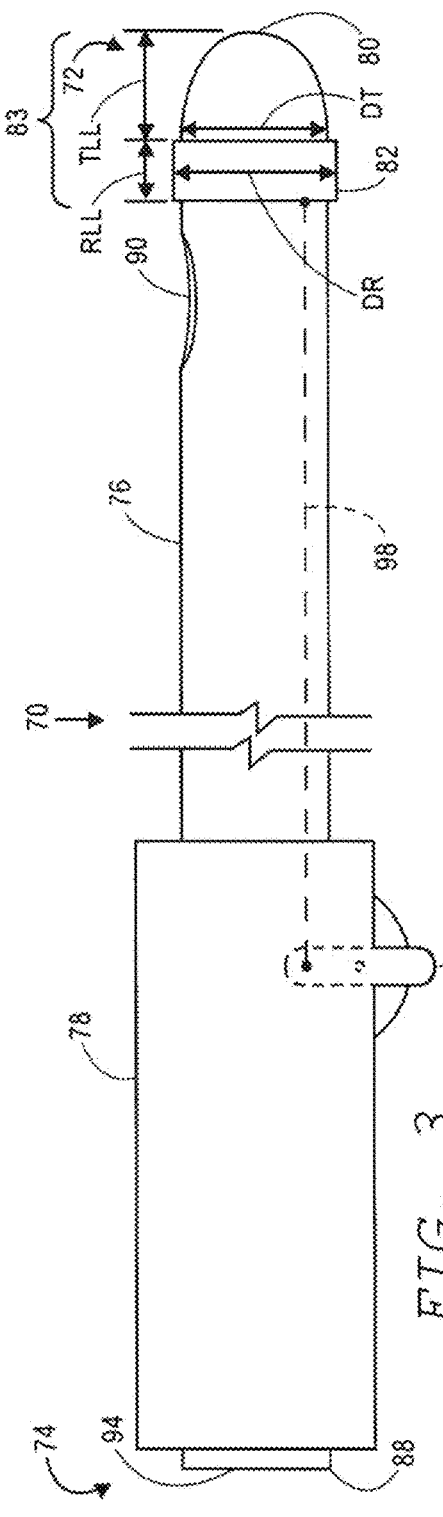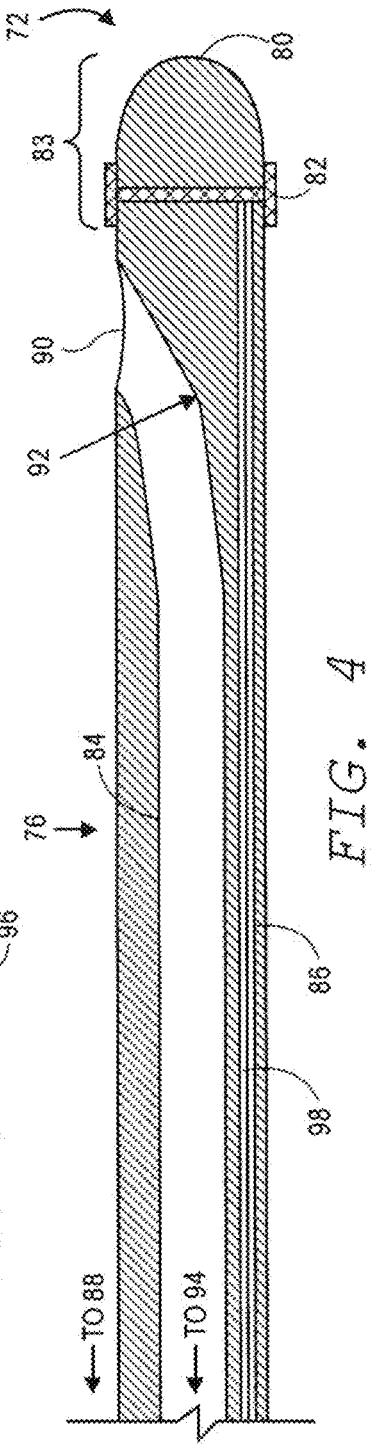
FIG. 2
FIG. 3
FIG. 4

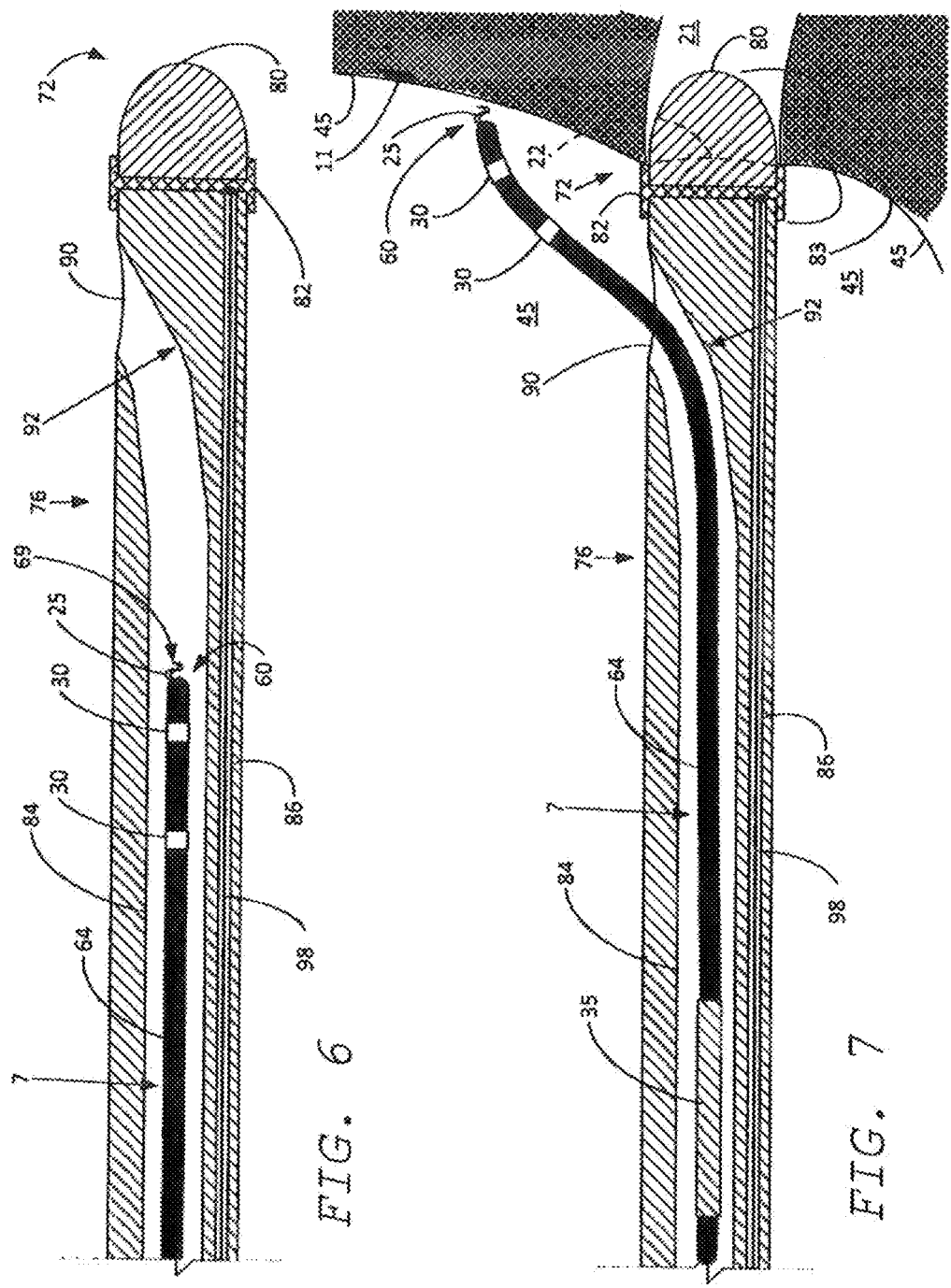

CORONARY SINUS-ANCHORED SHEATH FOR DELIVERY OF HIS BUNDLE PACING LEAD

PRIORITY

This patent application is a continuation of U.S. Non-Provisional patent application Ser. No. 15/900,558, filed Feb. 20, 2018, entitled "CORONARY SINUS-ANCHORED SHEATH FOR DELIVERY OF HIS BUNDLE PACING LEAD," which claims the benefit of priority to U.S. Provisional Patent Application No. 62/468,829, filed Mar. 8, 2017, entitled, "CORONARY SINUS-ANCHORED SHEATH FOR DELIVERY OF HIS BUNDLE PACING LEAD," and the contents of those applications are incorporated by reference herein in their entirety.

FIELD OF THE INVENTION

Aspects of the present invention relate to medical apparatus and methods. More specifically, the present invention relates to devices for, and methods of, delivering a lead for His bundle pacing.

BACKGROUND OF THE INVENTION

His bundle pacing has been shown to provide physiologically optimal ventricular stimulation, promoting atrioventricular and interventricular synchrony. However, identification of the endocardial pacing site of the His bundle is nontrivial, as the anatomy is patient-specific.

Traditionally, a mapping catheter is first used to identify the His bundle. Once the His bundle has been identified, the pacing lead must then be deployed to that same exact site. Unfortunately, this challenge is magnified by the difference between the approach angle of the mapping catheter, which accesses via the inferior vena cava ("IVC"), and that of the pacing lead, which accesses via the superior vena cava ("SVC").

There is a need in the art for devices that reduce the difficulty of accurately identifying the His bundle and delivering a pacing lead to the identified target site. There is also a need in the art for associated delivery methods.

BRIEF SUMMARY OF THE INVENTION

Disclosed herein is a catheter and related methods for delivering a His bundle pacing lead. Instead of using a mapping catheter to identify the His bundle and then independently navigating a pacing lead to that exact site, this His bundle pacing lead delivery catheter and methodology allows mapping to be performed by the pacing lead itself, followed by immediate fixation at the site of interest and removal of the catheter. The control and stability necessary for the pacing lead to be reliably guided to the His bundle is made possible by an atraumatic anchoring structure at a distal end of the catheter that can pivotally anchor to the coronary sinus ostium ("OS") and/or coronary sinus ("CS"). The catheter can be pivoted on the OS and/or CS while the lead distal region projects from a side opening in the catheter body. The lead body shape is adjusted by a stylet extending therethrough to vary the radius of the lead distal end from the pivot point provided by the OS and/or CS as the lead distal end is rotated about the pivot point via rotation of the catheter about the pivot point. Thus, the lead distal end can be used to cover a wide and varying swath of the right atrium ("RA") in mapping to identify the location of the His bundle.

The lead delivery system and associated methodology disclosed herein is advantageous as it allows for successful His bundle pacing via reliable identification of the optimal pacing site, as well as simple, in-line deployment of the pacing lead.

Also disclosed herein is a catheter for delivering an implantable medical lead to an implantation site near an ostium leading to a proximal region of a coronary sinus. In one embodiment, the catheter includes a distal end, a proximal end opposite the distal end, and a tubular body extending between the distal and proximal ends. The distal end is adapted to passively or actively pivotally anchor in the right atrium. A lead receiving lumen extends along the tubular body from the proximal end to an opening defined in a side of the tubular body near the distal end and proximal a distal termination of the distal end.

In one embodiment, the lead receiving lumen includes at least a ramped or curved portion proximal the opening. This ramped or curved portion causes the implantable medical lead to project from the opening laterally relative a longitudinal axis of the tubular body when the implantable medical lead is caused to extend from the opening.

In certain embodiments, the lead receiving lumen includes an extension that projects radially outward from the tubular body a distance of between approximately 2 mm and approximately 20 mm. Such an embodiment may further include a deflection member such that the extension is deflectable via movement of the deflection member.

In one embodiment where the distal end is adapted to passively anchor in the right atrium, there is an atraumatic fixation structure defining the distal termination of the distal end. The atraumatic fixation structure is configured to enter the ostium and passively pivotally anchor with the proximal region of the coronary sinus.

In one embodiment, the atraumatic fixation structure includes a distally tapering tip and a fixation ring proximal the distally tapering tip. The distally tapering tip distally extends from the fixation ring and the tubular body proximally extends from the fixation ring. The distally tapering tip is configured to pass through the ostium to be received in the proximal region of the coronary sinus. The fixation ring has a diameter that is larger than a greatest diameter of the distally tapering tip. The fixation ring is configured to limit the extent to which the distally tapering tip can extend into the proximal region of the coronary sinus. The distally tapering tip may include a bullnose shape.

In one embodiment where the distal end is adapted to actively anchor in the right atrium, there is an anchor needle distally extending from the distal termination of the distal end. In one embodiment, the anchor needle can be actuated between a distally extended state and a recessed state. The anchor needle distally extends from the distal termination when in the extended state. The anchor needle is being fully recessed within the distal end when in the recessed state.

In one embodiment, the anchor needle includes a sharp end of a stylet routed through the catheter.

In one embodiment, the anchor needle may have a diameter of between approximately 0.001 inch and approximately 0.015 inch. The anchor needle may distally project from the distal termination by a length of between approximately 2 mm and approximately 3 mm when fully distally extended from the distal termination.

In one embodiment, the catheter further includes a control handle and a deflection member. The control handle is operably coupled to the proximal end. The deflection member is displaceable via operation of the control handle. Displacement of the deflection member results in deflection of the distal end.

In one embodiment, the catheter is configured to be deflected by application of external sheaths to the catheter and/or application of internal guidewires and/or stylets to the catheter.

Also disclosed herein is a method of implanting an implantable medical lead for His bundle pacing. In one embodiment, the method includes: establishing a pivotable fixation between a right atrium and a distal termination of a distal end of a tubular body of a catheter, the fixation being passive or active; and with a distal region of an implantable lead extending from an opening defined in a side of the tubular body near the distal end and proximal the distal termination, pivoting the distal termination at the pivotable fixation to thereby cause the distal region of the implantable lead to sweep through an arc of rotation about the pivotable fixation.

The method may also include deflecting the distal region of the implantable lead to vary a radius between a distal tip of the implantable lead relative to the pivotable fixation. The deflection of the distal region may be brought about by application of at least one of a guidewire or stylet internally to the implantable lead. The method may also include sensing for a location of the His bundle with an electrode of the distal region of the implantable lead. Upon identifying the location of the His bundle, the implantable lead may be implanted at the location. Upon implantation of the lead, the catheter can be removed from about the implanted lead.

In one embodiment, the arc of rotation about the pivotable fixation is 360 degrees.

In one embodiment wherein the pivotable fixation is passive, the method may further include establishing the pivotable fixation at at least one of a coronary sinus ostium or a proximal region of a coronary sinus by atraumatically pivotally anchoring an atraumatic fixation structure to at least one of the coronary sinus ostium or the proximal region of the coronary sinus, the atraumatic fixation structure defining the distal termination of the distal end of the tubular body of the catheter.

The atraumatic fixation structure may include a distally tapering tip and a fixation ring proximal the distally tapering tip. The distally tapering tip passes through the ostium and into the proximal region of the coronary sinus. The fixation ring limits the extent to which the distally tapering tip extends into the proximal region of the coronary sinus.

In one embodiment wherein the pivotable fixation is active, the method may further include establishing the pivotable fixation with the right atrium tissue by anchoring an anchor needle to the right atrium tissue. Specifically, the anchor needle distally extends from the distal termination of the distal end of the tubular body of the catheter.

In one embodiment, the anchor needle may include a sharp distal end of a stylet extended through a lumen of the catheter.

In one embodiment, the anchor needle is fully recessed within the catheter until reaching the right atrium at which time the anchor needle is distally extended for insertion into tissue of the right atrium.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure.

Accordingly, the drawings and detailed description are to be regarded as illustrative in nature and not restrictive.

BRIEF DESCRIPTION OF THE DRAWINGS

FIG. 2 is a longitudinal side view of the RA lead of FIG. 1.

FIG. 3 is a longitudinal side view of an embodiment of a guide catheter.

FIG. 4 is a longitudinal cross section of a distal portion of the tubular body of the guide catheter of FIG. 2.

FIG. 6 is the same view of the catheter of FIG. 4, except showing the RA lead located in the central lead-receiving lumen of the catheter.

FIG. 7 is the same view as FIG. 6, except showing the atraumatic passive fixation arrangement of the distal end of the catheter atraumatically fixed to the OS and/or CS, and the distal end of the RA lead having exited the side opening of the delivery catheter to begin the mapping process.

DETAILED DESCRIPTION

Figure 1:
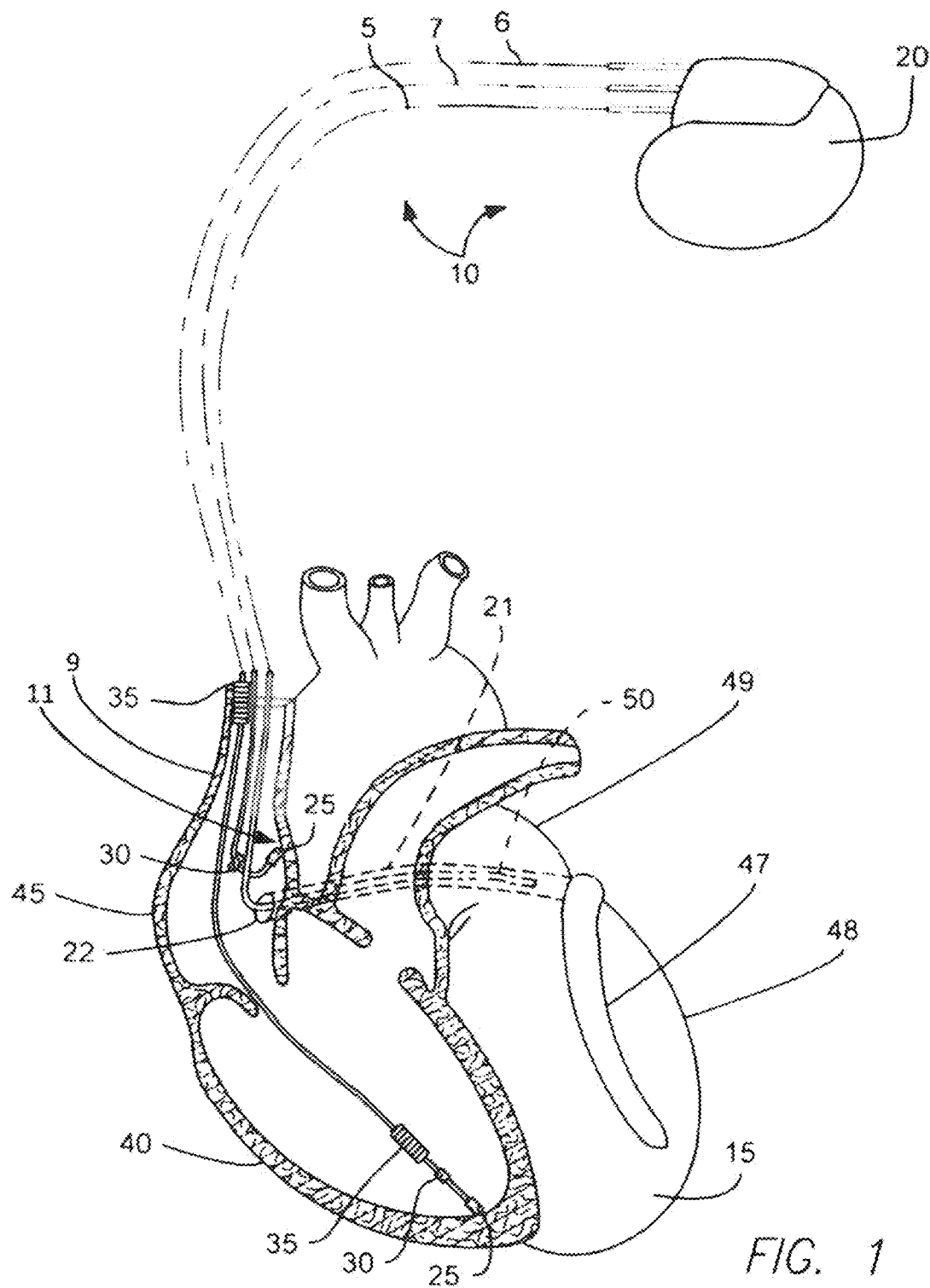
FIG. 1 is a diagrammatic depiction of an electrotherapy system electrically coupled to a patient heart as shown in an anterior view.

Implementations of the present disclosure involve a catheter 70 and associated methods for delivering His bundle pacing leads 7. In one embodiment, the distal end 72 of the catheter 70 includes an atraumatic distal tip 80 and fixation structure 83 that anchors to the coronary sinus ostium ("OS") 22 and/or coronary sinus ("CS") 21. An angled exit opening or port 90 exits the catheter tubular body 76 just proximal to a fixation ring 82 of the atraumatic fixation structure 83. Once the catheter 70 is anchored to the OS and/or CS, the pacing lead 7 can pass through the proximal exit port 90.

Efficient mapping of the His bundle 11 can be achieved by using the lead 7 to map the right atrium ("RA") 45 while the lead distal end 60 extends from the catheter body opening 90 with the atraumatic fixation structure 83 of the catheter 70 anchored to the OS" 22 and/or CS 21. Specifically, a stylet 94 within the lead 7 is used to alter the shape of the pacing lead to vary the radius distance of the lead distal end 60 from the anchor point at the OS and/or CS. Simultaneously, the catheter 70 can be rotated 360° about the anchor point provided by the OS and/or CS to give a wide swath of radial search angles.

Once the His bundle 11 is identified via the electrodes of the distal region of the lead 7 via this described methodology, the active fixation helical anchor 69 of the pacing lead 7 can be screwed into the cardiac tissue at the His bundle 11. The catheter 70 can then be removed by splitting and/or peeling the catheter away from about the implanted lead 7.

A similar methodology can be employed with another embodiment of the catheter 70, wherein the catheter employs an anchor needle 100 distally projecting from the atraumatic distal tip 80 of the catheter distal end 72. Upon delivery of the catheter distal tip 80 to a location in the RA 45, the anchor needle 100 is caused to project from the distal tip and penetrate into cardiac tissue of the RA 45 to act as an anchor location off of which the lead 7 may then be deployed to map the RA as discussed above. Thus, with this second embodiment, the catheter distal end 72 need not be anchored to the OS and/or CS, but may be anchored anywhere in the RA via the deployable anchor needle.

To begin a general, non-limiting discussion regarding some candidate electrotherapy arrangements employing His pacing, reference is made to FIG. 1, which is a diagrammatic depiction of an electrotherapy system 10 electrically coupled to a patient heart 15 as shown in an anterior view. As shown in FIG. 1, the system 10 includes an implantable pulse generator (e.g., pacemaker, implantable cardioverter defibrillator ("ICD"), or etc.) 20 and one or more (e.g., three) implantable medical leads 5, 6, 7 electrically coupling the patient heart 15 to the pulse generator 10. The following discussion focuses on possible His bundle pacing configurations, including the implantation of the His bundle (or right artrial ("RA")) lead 7 extending from the superior vena cava ("SVC") 9 into the right atrium 45 of the patient heart 15, the RA lead 7 being specifically implanted to pace the His bundle 11.

Depending on the patient electrotherapy needs, His bundle pacing may require that the system 10 employ only the RA lead 7 or the RA lead 7 with other leads, as indicated in FIG. 1. For example, in addition to the RA lead 7, the system 10 may further include a left ventricular ("LV") lead 5 extending into the coronary sinus ("CS") 21 via the coronary sinus ostium ("OS") 22. The CS 21 extends generally patient right to patient left from the OS 22 and, further, posterior to anterior until transitioning into the great cardiac vein 47, which then extends in a generally inferior direction along the anterior region of the left ventricle ("LV") 48. In extending generally posterior to anterior from the OS 22 until transitioning into the great cardiac vein 47, the CS 22 is inferior to the left atrium ("LA") 49 and superior to the LV 48.

Additionally or alternatively to the LV lead 5, the system 10 may also employ a right ventricular ("RV") lead 6. The RV and RA leads 6, 7 may employ pacing electrodes 25, sensing electrodes 30 and shock coils 35 as known in the art to respectively provide electrical stimulation to the right ventricle 40 and right atrium 45 of the heart 15. Although not illustrated in FIG. 1, the LV lead 5 may also employ pacing electrodes, sensing electrodes and shock coils the same or similar to those depicted with respect to the RV and RA leads 6, 7.

To begin a discussion of a system for efficiently implanting the RA lead 7 at the His bundle 11 to allow for His bundle pacing, reference is first made to FIG. 2, which is a longitudinal side view of the RA lead 7 of FIG. 1. As shown in FIG. 2 and as can also be understood from FIG. 1, the RA lead 7 includes a distal end 60, a proximal end 62 opposite the distal end, and a tubular body 64 that extends between the two ends 60, 62. The tubular body may have a construction configuration and be made from materials known in the art.

As depicted in FIG. 2, the RA lead 7 includes a lead connector end 66 at the proximal end 62. The lead connector end 66 may be of an IS1/DF1, IS4/DF4, or other configuration. As shown in FIG. 1, the lead connector end is adapted to be received in a receptacle of the implantable pulse generator 20 in a fluid-tight manner. As illustrated in FIG. 2, the lead connector end 66 includes one or more electrical contacts 67A-D and one or more electrically insulating portions 68A-D. The electrical contacts may be in the form of ring contacts 67A-C and/or a pin contact 67D. The electrical contacts and insulating portions are made from materials known in the art.

As can be understood from FIG. 2, a fixation arrangement 69 may be located at the distal end 60. The fixation arrangement 69 may be in the form of a passive fixation arrangement and/or an active fixation arrangement, such as, for example, a helical tissue anchor 68 that may be screwed into cardiac tissue.

As can be understood from FIGS. 1 and 2, the RA lead 7 may include a number of different types of electrodes. For example, the RA lead 7 may have a tip electrode 25, one or more ring electrodes 30 distal the tip electrode, and defibrillation shock coil 35 distal the ring electrodes. The tip electrode 25 may be include or be the helical tissue anchor 68. As known in the art, electrical conductors extend as helical coils, multi-filar conductors, or etc. through the tubular body 64 from the electrodes 25, 30, 35 to respective electrical contacts 67A-D of the lead connector end 66. Thus, electrical signals to and from the cardiac tissue are transmitted from the electrodes to the circuits of the implantable pulse generator 20.

To begin a discussion of a delivery tool that allows the RA lead 7 of FIG. 2 to be implanted for His pacing, reference is now made to FIG. 3, which is a longitudinal side view of an embodiment of a guide catheter 70. As shown in FIG. 3, the guide catheter 70 includes a distal end 72, a proximal end 74 opposite the distal end, a tubular body 76 that extends between the two ends 60, 62, and a handle portion 78 that is supported on a proximal region of the tubular body near the proximal end. The tubular body and handle may have a construction configuration and be made from materials known in the art. The catheter and its tubular body may have a one-to-one torque transfer.

As can be understood from FIG. 3 and also FIG. 4, which is a longitudinal cross section of a distal portion of the tubular body 76 of the guide catheter 70 of FIG. 2, the tubular body includes a distal tip 80, a fixation ring 82, a central lead-receiving lumen 84, one or more deflection lumens 86, and proximal termination 88. The tip 80 distally tapers and, in some embodiments, is of a bullnose shape. The distal tip 80 and the fixation ring 82 combine to form an atraumatic passive fixation arrangement 83 for passive fixation with the OS 22 and/or the very proximal aspect of the CS 21 just distal the OS 22, as discussed in greater detail below with respect to FIGS. 5, 7 and 8. In one embodiment, the fixation ring 82 and/or distal tip 80 also act as radiopaque markers and may be formed from radiopaque materials known in the art.

As reflected in FIG. 3, in one embodiment, the tubular body 76 of the catheter 70 at the distal tip 80 has a diameter DT of between approximately 2 mm and approximately 6 mm, while the fixation ring has a diameter DR of between approximately 4 mm and approximately 14 mm. In one embodiment, the diameter DR of the fixation ring 82 exceeds the diameter DT of the distal tip 80 by between approximately 2 mm and approximately 10 mm. In one embodiment, the distal tip 80 has a longitudinal length TLL of between approximately 5 mm and approximately 20 mm, and the fixation ring 82 has a longitudinal length RLL of between approximately 5 mm and approximately 20 mm.

As can be understood from FIGS. 3 and 4, the central lead-receiving lumen 84 terminates distally through the side of the catheter tubular body 76 just distal the fixation ring 82 as a distal side opening 90. In one embodiment, the lumen 84 extends coaxially along the central longitudinal axis of the tubular body 76 and, as it nears the side opening 90, the lumen 84 begins to bend or curve towards the exterior of the tubular body 76 to daylight as the side opening 90. Thus, a bend or curve 92 in the lumen 84 creates a ramp or deflection point 92 that causes the RA lead 7 to project laterally away from the catheter tubular body 76 via the opening 90 when the RA lead 7 is routed through and distally out of the catheter central lead-receiving lumen 84, as discussed in detail below with respect to FIGS. 5, 7 and 8.

The central lead-receiving lumen 84 proximally daylights as a proximal opening 94 at the proximal termination of the catheter tubular body 76. It is via this proximal opening 94 that the RA lead 7 can be loaded into the lumen 84 to be distally displaced down the lumen 84.

As illustrated in FIG. 3, the handle 78 includes a deflection mechanism 96 that is pivotally or slideably coupled to the rest of the handle 78. The deflection mechanism 96 is attached to one or more deflection members 98, which may be in the form of wires. These one or more deflection members respectively extend through the one or more deflection lumens 86 to couple to a structural aspect of the distal end 72 of the catheter tubular body 76. For example, this structural aspect may be the fixation ring 82. In use, a medical professional's digit may act against a lever, knob or button of the deflection mechanism 96 to cause the one or more deflection members 98 to distally-proximally displace within the respective deflection lumens 86 to cause the catheter distal end 72 to deflect laterally, thereby resulting in steering of the catheter distal end. The deflection provided by the deflection member(s) 98 may be single directional, bi-directional, or in even more direction, depending on the number of deflection members and their arrangement.

While the catheter 70 of FIGS. 3 and 4 is described in the context of being steerable via a control handle 78 that is capable of deflecting the catheter distal end 72 via a deflection mechanism 96 and its deflection member(s) 98, in other embodiments, the catheter may simply be configured for deflection by use of external sheaths and/or internal stylets and/or guidewires.

In some embodiments, the catheter tubular body 76 and the handle 78 may be configured to be longitudinally opened along the entirety of their respective lengths to allow for removal from about the RA lead 7 once implanted. Depending on the embodiment, the body 76 and handle 78 may be capable of being split or pealed via arrangements and methods known in the art.

Figure 5:
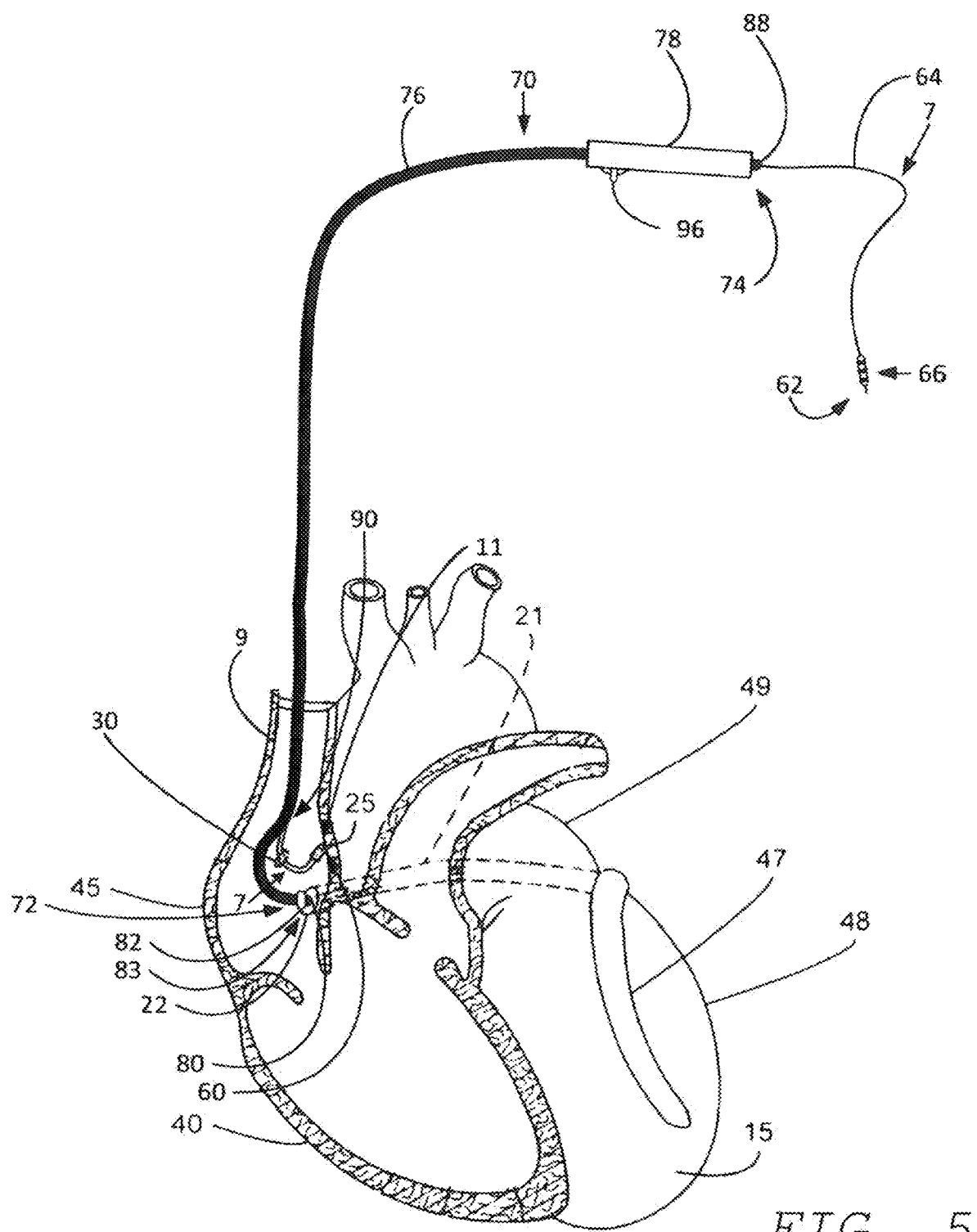
FIG. 5 is the same view as FIG. 1, except showing the RA lead being delivered to the RA via the delivery catheter, the distal tip of the catheter being fixed to the OS and/or CS to allow the RA lead to extend from the catheter and be used to map in locating the His bundle.

To begin a discussion of a method of delivering the RA lead 7 via the delivery catheter 70 to or near the His bundle 11 for His pacing and bracing the RA lead off of the catheter to use the RA lead to map in locating the His bundle 11, reference is made to FIG. 5, which is the same view as FIG. 1, except showing the RA lead 7 being delivered to the RA 45 via the delivery catheter 70. As shown in FIG. 5, the delivery catheter 70 has been tracked through the SVC 9 and into the RA 45 such that the atraumatic passive fixation arrangement 83 of the distal end 72 of the catheter is passively fixed to the OS 22 and/or CS 21, as discussed in detail below. With the catheter 70 so braced off of the OS and/or CS, the RA lead 7 can be extended from the catheter 70 to map the RA 45 to identify the location of the His bundle 11. Once the His bundle is located, the RA lead distal end can then be implanted at the identified site by screwing the anchor into the cardiac tissue of the identified site.

As can be understood from FIG. 5 and also FIG. 6, which is the same view of the catheter of FIG. 4, except showing the RA lead 7 located in the central lead-receiving lumen 84 of the catheter 70, the RA lead 7 can be present in the delivery catheter 70 as the catheter is being tracked into position for atraumatic passive fixation to the OS 22 and/or CS 21. Alternatively, the RA lead 7 can be inserted into the catheter 70 once the atraumatic passive fixation arrangement 83 of the distal end 72 of the catheter is passively fixed to the OS and/or CS. In either case, the RA lead 7 extends through the catheter body 76 via the lumen 84.

As can be understood from FIGS. 3 and 5, in the process of tracking the catheter distal end 72 to the OS 22 and/or CS 21, the medical professional grasps the catheter handle 78 and deflects the distal end 72 via actuation of the deflection mechanism 96. The lead body 64 of the RA lead 7 extends proximally from the distal termination 88 of the catheter body and the catheter proximal end 74 to proximally extend to the lead proximal end 62 and its lead connector end 66. As illustrated in FIG. 6, the lead distal end 60 typically remains recessed within the confines of the delivery catheter 70 until the catheter distal end 72 is atraumatically fixed to the OS 22 and/or CS 21 via the atraumatic passive fixation arrangement 83 of the distal end 72 of the catheter 70. The pacing lead 7 is fed through the lumen 84 of the catheter 70 until the lead distal tip 80 is fluoroscopically visible outside the angled exit port or side opening 90.

FIG. 7 is the same view as FIG. 6, except showing the atraumatic passive fixation arrangement 83 of the distal end 72 of the catheter 70 atraumatically fixed to the OS 22 and/or CS 21, and the distal end 60 of the RA lead 7 having exited the side opening 90 of the delivery catheter 70 to begin the mapping process. As can be understood from FIGS. 5 and 7, once the catheter tip 80 of the catheter distal end 72 is atraumatically fixed to the OS 22 and/or CS 21 near the His bundle 11, the RA lead 7 can be distally displaced relative to the catheter 70 to cause the lead distal end 60 to extend from the side opening 90 in the lead body. Because of the curvature of the ramp 92 of the catheter central lumen 84, the lead distal end 60 projects substantially laterally or orthogonally relatively to the longitudinal center axis of the catheter body when the lead distal end has exited the side opening 90.

As can be understood from FIG. 7, in one embodiment, the atraumatic passive fixation arrangement 83 of the distal end 72 of the catheter 70 atraumatically engages the OS 22 and/or CS 21. For example, the atraumatic passive fixation arrangement 83 may be said to form an interference fit with the OS 22 and/or CS 21. Specifically, the distal tip 80 is received within the OS 22 and/or CS 21, thereby preventing side-to-side displacement of the distal tip 80 relative to the OS and CS. At the same time, the fixation ring 82 is of sufficiently large diameter that the ring 82 is limited to the extent to which it can pass through the OS 22 and extend down the CS 21. Thus, the atraumatic passive fixation arrangement 83 sufficiently enters the OS 22 and CS 21 to prevent side-to-side displacement of the catheter distal end 72 relative to the RA 45 and dislodgement from the OS and CS, but is of sufficient diameter to be prevented from overextension distally down the CS.

Thus, as can be understood from FIG. 7, the structure of the atraumatic passive fixation arrangement 83 of the distal end 72 of the catheter 70 does not allow the catheter distal end 72 to enter the OS 22 or CS 21 beyond a predefined length. This guarantees that the proximal pacing lead exit port or opening 90 remains in the RA 45 and not in the CS 21. In one embodiment, the tapered distal tip 80 of the atraumatic passive fixation arrangement 83 of the distal end 72 of the catheter 70 is designed to rest just inside the OS and CS to establish a stable anchoring point. Anchoring the catheter distal end 72, and thus the lead 7, to a structure in the RA 45 facilitates the manual search for the His bundle 11 by virtually eliminating the relative movement of the His bundle with each heart contraction. Despite intracardiac anatomic variability, the His bundle 11 is typically located near the OS 22.

Figure 8:
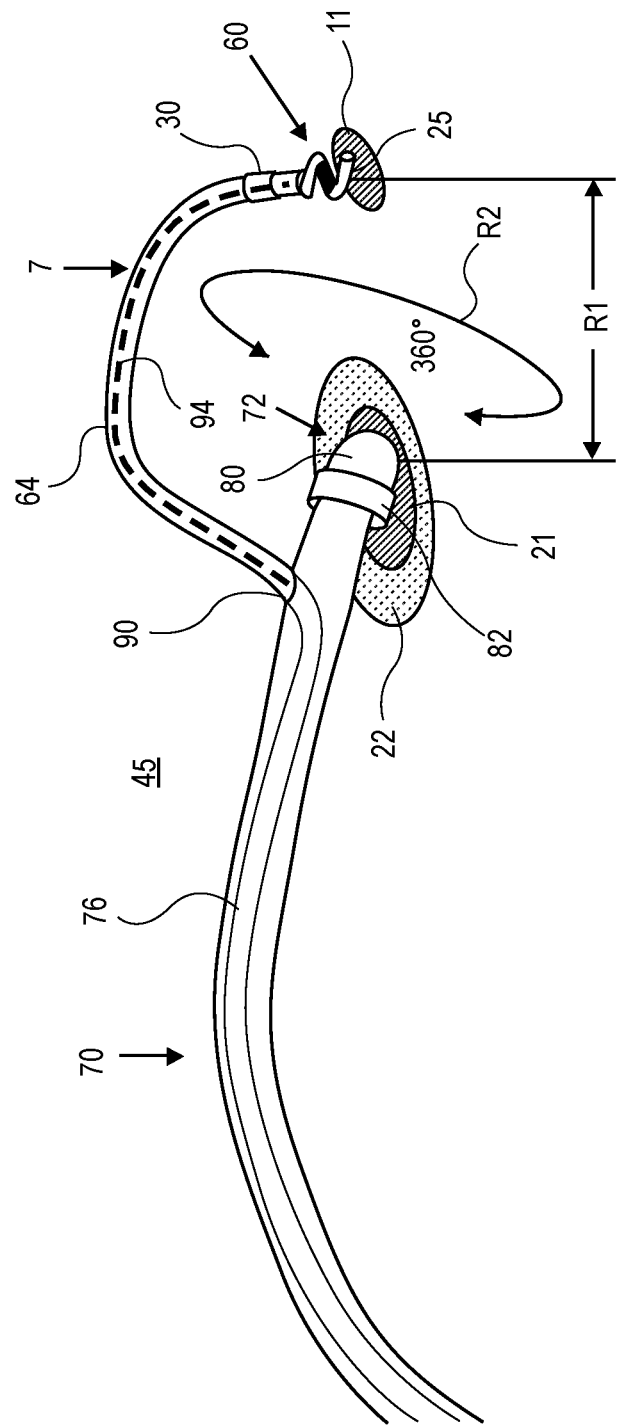
FIG. 8 is perspective view of the atraumatic passive fixation arrangement of the catheter atraumatically fixed to the OS and/or CS, and the distal end of the RA lead having exited the side opening of the delivery catheter and being used to map for the location of the His bundle.

FIG. 8 is perspective view of the atraumatic passive fixation arrangement 83 of the catheter 70 atraumatically fixed to the OS 22 and/or CS 21, and the distal end 60 of the RA lead 7 having exited the side opening 90 of the delivery catheter 70 and being used to map for the location of the His bundle 11. As can be understood from FIG. 8, efficient mapping of the His bundle 11 can be achieved by using the lead 7 to map the right atrium ("RA") 45 while the lead distal end 60 extends from the catheter body opening 90 with the atraumatic fixation structure 83 of the catheter 70 anchored to the OS" 22 and/or CS 21. Specifically, a stylet 94 within the lead 7 is used to alter the shape of the pacing lead to vary the radius distance R1 of the lead distal end 60 from the anchor point at the OS and/or CS. Thus, the use of stylets 94 with formable distal tips in the pacing lead lumen provides control over the distance between the CS anchoring point 21 and the interface between the lead distal end 60 and endocardium, this distance being the search or mapping radius R1 of FIG. 8.

Simultaneously with the stylet-enabled control of the search radius of the lead distal end, the catheter 70 can be rotated an angle of rotation R2 of 360° about the anchor point provided by the OS and/or CS to give a wide swath of radial search angles. Specifically, the rotation of the entire catheter 70 from the proximal handle 78 outside the patient body with a one-to-one torque transfer enables rotation of the exit port 90, and thus control over the approach angle of the pacing lead 7 from the CS anchor location 21, this rotation being the rotational search angle R2 of FIG. 8.

Once the His bundle 11 is identified via the electrodes of the distal region of the lead 7 via this methodology described with respect to FIG. 8, the active fixation helical anchor 69 of the pacing lead 7 can be screwed into the cardiac tissue at the His bundle 11. The catheter 70 can then be removed by splitting and/or peeling the catheter away from about the implanted lead 7.

Figure 9:
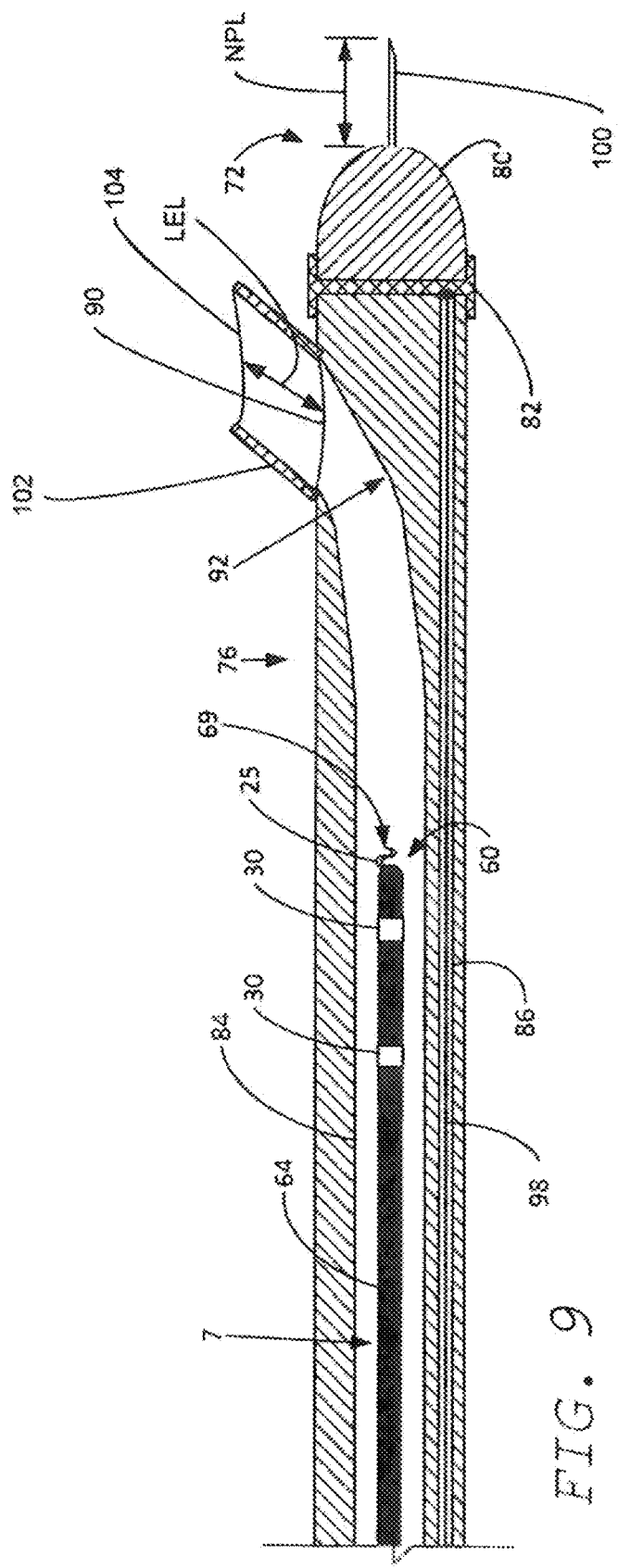
FIG. 9 is the same view as FIG. 6, except of another embodiment of the catheter, which is equipped with an anchor needle at the distal tip.

While the above discussed methodology takes place in the context of the catheter distal end 72 being anchored with the OS and/or CS, in other embodiments of the system disclosed herein, the catheter distal end 72 may be configured to anchor to tissue anywhere in the RA. For example, as shown in FIG. 9, which is the same view as FIG. 6, except of another embodiment of the catheter 70, the catheter 70 is equipped with a selectively deployable anchor needle 100 at the distal end 72. The anchor needle 100 may be configured such that it remains recessed within the atraumatic distal tip 80 until ready to be deployed into cardiac tissue of the RA 45 for purposes of providing a tissue anchor point off of which the lead 7 is used to map the RA for the location of the His bundle.

In certain embodiments, a screw is used instead of or in addition to needle 100. In certain embodiments, needle 100 and/or a screw may be retractable into catheter 70, such that catheter 70 may be moved by retracting the needle 100 and/or the screw.

In certain embodiments, an obturator may be used U.S. Pat. No. 7,056,314, incorporated herein by reference in its entirety, to facilitate the delivery of catheter 70.

In one embodiment, the anchor needle may have a threaded or other rotationally actuated mechanical arrangement within the catheter distal end 72. Thus, the anchor needle 100 may be caused to extend from, or retract into, the distal tip 80 via rotation of a stylet extending through the catheter body via a lumen and engaging the rotationally actuated mechanical arrangement of the anchor needle.

Alternatively, the anchor needle 100 may be biased to be recessed within the confines of the distal tip 80. Accordingly, a stylet may be extended through a lumen of the catheter to force the anchor needle to project distally from the distal tip 80.

In another embodiment, the anchor needle may simply be caused to selectively extend from, or retract into, the distal tip 80 via action of the stylet or other tool upon the proximal end of the anchor needle.

Finally, in one embodiment, the anchor needle 100 may be a sharp distal end of the stylet, which is routed through a lumen of the catheter to be caused to distally project from the distal tip 80 or be retracted within the confines of the distal tip 80.

In one embodiment, the anchor needle 100 may have a diameter of between approximately 0.001 inch and approximately 0.015 inch. When fully distally extended from the distal tip 80 of the catheter as shown in FIG. 9, the anchor needle 100 may have a needle projection length ("NPL") of between approximately 2 mm and approximately 3 mm.

Similar to the methodology described above with respect to atraumatically anchoring to the OS and/or CS, the embodiment depicted in FIG. 9 can anchored to a point in the RA 45 to map the RA to identify the His bundle location and then implant the lead distal end at the identified location. Specifically, the catheter distal end 72 is tracked into the RA 45 with the anchor needle 100 recessed within the confines of the distal end 72 to avoid causing damage to cardiac and vessel structures and tissue. Upon approaching a desired anchoring location in the RA 45, the anchor needle 100 is caused to distally project the full NPL from the distal tip 80, as illustrated in FIG. 9. The fully deployed anchor needle 100 is then imbedded in the cardiac tissue at the desired anchoring location in the RA 45. The lead 7 can then be caused to exit the side opening 90 of the catheter 70 to map the RA to identify the location of the His bundle. The catheter 70 can be rotated about the tissue anchored needle 100 in the process of sweeping the lead electrodes along the RA tissue to find the His bundle, much like the process that is described above with respect to atraumatically anchoring off of the OS and/or CS. The rest of the lead implantation process and catheter removal process takes place as discussed above.

As can be understood from FIG. 9, in certain embodiments, the catheter 70 may be equipped with a lumen extension 102 that extends radially outward of the catheter body exterior and what would otherwise be the exit opening or port 90 of the lumen 84 to result in a radially outward or extended exit opening or port 104. In some embodiments, this lumen extension 102 may have a lumen extension length ("LEL") of between approximately 2 mm and approximately 20 mm. The lumen extension 102 may facilitate the lateral projection of the lead 7 from the catheter 70.

In certain embodiments, the lumen extension 102 may be adapted to be routed through the venous return system of a patient. For example, lumen extension 102 may comprise a compliant structure. Lumen extension 102 may be adapted to fold when routed through a vein. In certain embodiments, lumen extension 102 may be adapted to fold in order to lay against catheter 70, such that it may be routed using, for example, an implantable sheath.

In one embodiment, the lumen extension 102 may be deflectable via a deflection member similar to the deflection member 98 employed to deflect the catheter distal end 72. Thus, the lumen extension 102 can be steered relative to the rest of the catheter to further guide the lead distal end, and the electrodes supported thereon, in sweeping the RA in the course of mapping the RA. While the lumen extension 102 is depicted in the context of the embodiment of FIG. 9, such a feature could be employed with the embodiment of FIGS. 3-8.

While the term catheter is employed herein to describe a tubular device for implantable lead delivery, the term catheter is intended to also encompass other types of tubular bodies adapted for delivery of implantable medical leads, including sheaths. Thus, the term catheter should be interpreted as including both catheters and sheaths, and other tubular lead delivery devices and should not be otherwise limited in scope.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A lead delivery catheter, comprising:
   a tubular body extending along a longitudinal axis from a proximal end to a distal tip, wherein the distal tip includes an anchor needle having a needle axis coaxial with the longitudinal axis of the tubular body and a needle tip distal to the distal tip to actively pivotally anchor in tissue near an implantation site;
   an extension that projects outward at an angle to the longitudinal axis and the needle axis, wherein the extension extends from an exterior surface of the tubular body to an exit port, wherein the extension has a cylindrical wall over an extension length; and
   a lead lumen extending through the tubular body along the longitudinal axis and through the extension to the exit port.

2. The lead delivery catheter of claim 1 further comprising a fixation ring mounted on the tubular body proximal to the distal tip.

3. The lead delivery catheter of claim 2, wherein the fixation ring is mounted on the tubular body between the extension and the distal tip.

4. The lead delivery catheter of claim 2 further comprising a deflection member displaceable distally-proximally to deflect the distal tip laterally.

5. The lead delivery catheter of claim 4, wherein the deflection member is coupled to the fixation ring.

6. The lead delivery catheter of claim 1, wherein the distal tip includes a distally tapering tip.

7. A lead delivery system, comprising:
   a lead delivery catheter including
      a tubular body extending along a longitudinal axis from a proximal end to a distal tip, wherein the distal tip includes an anchor needle configured to actively pivotally anchor in tissue near an implantation site,
      an extension that projects outward from an exterior surface of the tubular body to an exit port, wherein the extension has a cylindrical wall over an extension length, and
      a lead lumen extending through the tubular body along the longitudinal axis and through the extension to the exit port; and
   a pacing lead configured to advance through the lead lumen and to project laterally through the exit port.

8. The lead delivery system of claim 7 further comprising a fixation ring mounted on the tubular body proximal to the distal tip.

9. The lead delivery system of claim 8, wherein the fixation ring is mounted on the tubular body between the extension and the distal tip.

10. The lead delivery system of claim 8 further comprising a deflection member displaceable distally-proximally to deflect the distal tip laterally.

11. The lead delivery system of claim 10, wherein the deflection member is coupled to the fixation ring.

12. The lead delivery system of claim 7, wherein the distal tip includes a distally tapering tip.

13. A method, comprising:
   anchoring a distal tip of a lead delivery catheter near an implantation site, wherein the lead delivery catheter includes a tubular body extending along a longitudinal axis from a proximal end to the distal tip, an extension that projects outward from an exterior surface of the tubular body, wherein the extension has a cylindrical wall over an extension length, and a lead lumen extending through the tubular body along the longitudinal axis and through the extension to the exit port of the extension; and
   pivoting the lead delivery catheter to cause the extension to sweep through an arc of rotation about the longitudinal axis such that the exit port is directed to the implantation site; and
   advancing a pacing lead through the lead lumen and the exit port to the implantation site.

14. The method of claim 13 further comprising deflecting the lead delivery catheter to vary a radius between a distal lead tip of the pacing lead relative to the distal tip of the lead delivery catheter.

15. The method of claim 13 further comprising sensing a location of a His bundle with an electrode of the pacing lead.

16. The method of claim 15 further comprising, upon identifying the location of the His bundle, implanting the pacing lead at the location.

17. The method of claim 13, wherein the distal tip includes a distally tapering tip configured to passively pivotally anchor in an ostium of a coronary sinus near the implantation site.

18. The method of claim 13, wherein the distal tip includes an anchor needle configured to actively pivotally anchor in tissue near the implantation site.

* * * * *